(12) United States Patent
MacDonald et al.

(10) Patent No.: US 8,225,729 B2
(45) Date of Patent: Jul. 24, 2012

(54) THREE-DIMENSIONAL WIPING SUBSTRATE AND METHOD THEREFOR

(75) Inventors: John Gavin MacDonald, Decatur, GA (US); Jaeho Kim, Roswell, GA (US); WanDuk Lee, Seoul (KR); Jin Heo, Yongin-si (KR); CholWon Koh, Suwon-si (KR); SangSoo Lee, Yongin-si (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 805 days.

(21) Appl. No.: 12/336,078

(22) Filed: Dec. 16, 2008

(65) Prior Publication Data

US 2010/0147203 A1 Jun. 17, 2010

(51) Int. Cl.
*D05B 23/00* (2006.01)
*B32B 3/06* (2006.01)
(52) U.S. Cl. .................. 112/475.08; 428/102
(58) Field of Classification Search ............. 112/475.01, 112/475.08, 475.14, 475.17, 475.18; 428/98–113, 428/152; 442/327, 328, 334
See application file for complete search history.

(56) References Cited

U.S. PATENT DOCUMENTS

| | | | |
|---|---|---|---|
| 2,681,032 A | 6/1954 | Shaw | |
| 2,813,501 A * | 11/1957 | Shotsky | 112/475.18 |
| 3,338,992 A | 8/1967 | Kinney | |
| 3,341,394 A | 9/1967 | Kinney | |
| 3,371,668 A | 3/1968 | Johnson | |
| 3,502,538 A | 3/1970 | Petersen | |
| 3,502,763 A | 3/1970 | Hartmann | |
| 3,542,615 A | 11/1970 | Dobo et al. | |
| 3,556,932 A | 1/1971 | Coscia et al. | |
| 3,556,933 A | 1/1971 | Williams et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 4,246,900 A | 1/1981 | Schroder | |
| 4,340,563 A | 7/1982 | Appel et al. | |
| 4,357,938 A | 11/1982 | Ito et al. | |
| 4,447,240 A | 5/1984 | Ito et al. | |
| 4,488,928 A | 12/1984 | Ali Khan et al. | |
| 4,623,342 A | 11/1986 | Ito et al. | |
| 4,640,859 A | 2/1987 | Hansen et al. | |
| 4,675,394 A | 6/1987 | Solarek et al. | |
| 4,779,456 A | 10/1988 | Cantoni | |
| 4,781,731 A | 11/1988 | Schlinger | |
| 4,787,896 A | 11/1988 | Houghton et al. | |
| 4,809,493 A | 3/1989 | Genba et al. | |
| 4,834,733 A | 5/1989 | Huntoon et al. | |
| 4,942,089 A * | 7/1990 | Genba et al. | 428/364 |
| 4,981,557 A | 1/1991 | Bjorkquist | |
| 5,007,906 A | 4/1991 | Osborn, III et al. | |
| 5,008,344 A | 4/1991 | Bjorkquist | |
| 5,085,736 A | 2/1992 | Bjorkquist | |

(Continued)

FOREIGN PATENT DOCUMENTS

CN 3251084 8/2002

(Continued)

*Primary Examiner* — Ismael Izaguirre
(74) *Attorney, Agent, or Firm* — Denise L. Stoker; Kenya T. Pierre

(57) ABSTRACT

A planar substrate has a moisture activated shrinking filament applied thereon. When wetted, the shrinking filament shrinks and causes the planar substrate to gather and pucker. The planar substrate with the filament thereon may be compressed into a compact shape when in a dry state.

6 Claims, 4 Drawing Sheets

U.S. PATENT DOCUMENTS

| | | | |
|---|---|---|---|
| 5,176,672 A | 1/1993 | Bruemmer et al. | |
| 5,181,563 A | 1/1993 | Amaral | |
| 5,260,345 A | 11/1993 | Desmarais et al. | |
| 5,310,590 A * | 5/1994 | Tochacek et al. | 428/102 |
| 5,334,176 A | 8/1994 | Buenger et al. | |
| 5,397,316 A | 3/1995 | LaVon et al. | |
| 5,415,640 A | 5/1995 | Kirby et al. | |
| 5,447,507 A | 9/1995 | Yamamoto | |
| 5,514,121 A | 5/1996 | Roe et al. | |
| 5,520,674 A | 5/1996 | Lavon et al. | |
| 5,527,303 A | 6/1996 | Milby, Jr. et al. | |
| 5,575,785 A | 11/1996 | Gryskiewicz et al. | |
| 5,591,150 A | 1/1997 | Olsen et al. | |
| 5,779,860 A | 7/1998 | Hollenberg et al. | |
| 5,833,680 A | 11/1998 | Hartman | |
| 5,858,515 A | 1/1999 | Stokes et al. | |
| 5,997,520 A | 12/1999 | Ahr et al. | |
| 6,045,900 A | 4/2000 | Haffner et al. | |
| 6,071,580 A | 6/2000 | Bland et al. | |
| 6,114,597 A | 9/2000 | Romare | |
| 6,133,501 A | 10/2000 | Hallock et al. | |
| 6,168,583 B1 | 1/2001 | Tanji et al. | |
| 6,175,056 B1 | 1/2001 | Carlucci et al. | |
| D448,476 S | 9/2001 | Page et al. | |
| 6,293,935 B1 | 9/2001 | Kimura et al. | |
| D448,846 S | 10/2001 | Page et al. | |
| 6,296,628 B1 | 10/2001 | Mizutani | |
| 6,306,818 B1 | 10/2001 | Anderson et al. | |
| 6,315,765 B1 | 11/2001 | Datta et al. | |
| 6,326,525 B1 | 12/2001 | Hamajima et al. | |
| 6,346,097 B1 | 2/2002 | Blaney | |
| 6,348,047 B1 | 2/2002 | Harper | |
| 6,387,084 B1 | 5/2002 | VanGompel et al. | |
| 6,392,117 B1 | 5/2002 | Mayer et al. | |
| 6,429,261 B1 | 8/2002 | Lang et al. | |
| 6,432,097 B1 | 8/2002 | Ahr et al. | |
| 6,436,081 B1 | 8/2002 | Wada et al. | |
| 6,444,214 B1 | 9/2002 | Cole et al. | |
| 6,521,811 B1 | 2/2003 | Lassen et al. | |
| 6,537,663 B1 | 3/2003 | Chang et al. | |
| 6,548,592 B1 | 4/2003 | Lang et al. | |
| 6,551,297 B2 | 4/2003 | Tanaka et al. | |
| 6,579,570 B1 | 6/2003 | Lang et al. | |
| 6,585,712 B2 | 7/2003 | Yoshimasa | |
| 6,599,848 B1 | 7/2003 | Chen et al. | |
| 6,620,144 B1 | 9/2003 | Glasgow et al. | |
| 6,627,670 B2 | 9/2003 | Mork et al. | |
| 6,632,205 B1 | 10/2003 | Sauer | |
| 6,653,406 B1 | 11/2003 | Soerens et al. | |
| 6,664,436 B2 | 12/2003 | Topolkaraev et al. | |
| 6,666,850 B1 | 12/2003 | Ahr et al. | |
| 6,683,143 B1 | 1/2004 | Mumick et al. | |
| 6,713,414 B1 | 3/2004 | Pomplun et al. | |
| 6,727,004 B2 | 4/2004 | Goulet et al. | |
| 6,786,893 B2 | 9/2004 | Strand | |
| 6,815,502 B1 | 11/2004 | Chang et al. | |
| 6,840,925 B2 | 1/2005 | Mishima et al. | |
| 6,908,458 B1 | 6/2005 | Sauer et al. | |
| 6,958,430 B1 | 10/2005 | Marinelli | |
| D521,149 S | 5/2006 | Adams et al. | |
| 7,037,298 B2 | 5/2006 | Ohshima et al. | |
| 7,145,054 B2 | 12/2006 | Zander et al. | |
| 7,179,247 B2 | 2/2007 | Mizutani et al. | |
| 7,252,870 B2 | 8/2007 | Anderson et al. | |
| 7,314,967 B2 | 1/2008 | Ashton et al. | |
| D567,369 S | 4/2008 | Gilroy | |
| 7,358,282 B2 | 4/2008 | Krueger et al. | |
| 7,491,864 B2 | 2/2009 | Nishizawa et al. | |
| D600,802 S | 9/2009 | Hood et al. | |
| D600,803 S | 9/2009 | Hood et al. | |
| D600,805 S | 9/2009 | Hood et al. | |
| 7,621,899 B2 | 11/2009 | Fujikawa et al. | |
| 2001/0029359 A1 | 10/2001 | Carlucci | |
| 2003/0050614 A1 | 3/2003 | D'Acchioli et al. | |
| 2003/0163104 A1 | 8/2003 | Tears et al. | |
| 2004/0192142 A1* | 9/2004 | Zafiroglu et al. | 442/352 |
| 2004/0224593 A1* | 11/2004 | Strength et al. | 442/239 |
| 2005/0010185 A1 | 1/2005 | Mizutani et al. | |
| 2006/0116651 A1 | 6/2006 | Kurita et al. | |
| 2006/0148917 A1 | 7/2006 | Radwanski et al. | |
| 2006/0246272 A1 | 11/2006 | Zhang et al. | |
| 2006/0282059 A1 | 12/2006 | Fujikawa et al. | |
| 2006/0287635 A1 | 12/2006 | Angel | |
| 2007/0031667 A1 | 2/2007 | Hook et al. | |
| 2007/0043027 A1 | 2/2007 | Rueckle et al. | |
| 2007/0093772 A1 | 4/2007 | Koyama et al. | |
| 2007/0210011 A1 | 9/2007 | Hook | |
| 2007/0225671 A1 | 9/2007 | Angel | |
| 2007/0287973 A1 | 12/2007 | Cohen et al. | |
| 2008/0269703 A1 | 10/2008 | Collins et al. | |
| 2009/0036854 A1 | 2/2009 | Guidotti et al. | |
| 2009/0054760 A1 | 2/2009 | Burke | |
| 2009/0157022 A1 | 6/2009 | MacDonald et al. | |
| 2009/0157032 A1 | 6/2009 | MacDonald et al. | |
| 2009/0204095 A1 | 8/2009 | McDaniel | |
| 2009/0240220 A1 | 9/2009 | MacDonald et al. | |
| 2009/0299312 A1 | 12/2009 | MacDonald et al. | |
| 2009/0326495 A1 | 12/2009 | MacDonald et al. | |
| 2010/0152642 A1 | 6/2010 | Kim et al. | |
| 2010/0152690 A1 | 6/2010 | Ong et al. | |
| 2010/0152692 A1 | 6/2010 | Ong et al. | |
| 2010/0279057 A1* | 11/2010 | Zafiroglu | 428/86 |

FOREIGN PATENT DOCUMENTS

| | | |
|---|---|---|
| EP | 0 220 741 A2 | 5/1987 |
| EP | 0 554 565 A1 | 8/1993 |
| EP | 0 557 047 A1 | 8/1993 |
| EP | 0 815 821 A2 | 1/1998 |
| EP | 0 846 454 A1 | 6/1998 |
| EP | 0 910 321 A1 | 4/1999 |
| EP | 1 091 716 A2 | 4/2001 |
| EP | 1 206 923 A1 | 5/2002 |
| EP | 000772975-002 | 11/2008 |
| GB | 2 244 653 A | 12/1991 |
| GB | 2 078 590 | 2/1999 |
| JP | 02-107249 A | 4/1990 |
| JP | 03-185197 A | 8/1991 |
| JP | 08-299770 A | 11/1996 |
| JP | 09-041221 A | 2/1997 |
| JP | 2001-017467 A | 1/2001 |
| JP | 2004-041339 A | 2/2004 |
| JP | 1233575 S | 3/2005 |
| JP | 2006-334113 A | 12/2006 |
| JP | 1318295 S | 12/2007 |
| KR | 10-2006-0114359 A | 11/2006 |
| WO | WO 94/02095 | 2/1994 |
| WO | WO 95/25493 | 9/1995 |
| WO | WO 97/14389 A1 | 4/1997 |
| WO | WO 97/40798 A1 | 11/1997 |
| WO | WO 97/40803 A1 | 11/1997 |
| WO | WO 00/53830 A1 | 9/2000 |
| WO | WO 01/52713 A2 | 7/2001 |
| WO | WO 03/009876 A1 | 2/2003 |
| WO | WO 2004/009221 A1 | 1/2004 |
| WO | WO 2005/016103 A1 | 2/2005 |
| WO | WO 2006/021763 A1 | 3/2006 |
| WO | WO 2007/073254 A1 | 6/2007 |
| WO | WO 2007/125352 A1 | 11/2007 |

* cited by examiner

THREE-DIMENSIONAL WIPING SUBSTRATE AND METHOD THEREFOR

BACKGROUND

The present invention relates generally to wiping substrates, and in particular to wiping substrates that change from a substantially planar configuration to a three-dimensional configuration upon wetting.

Wet wipes are used for various applications such as cleaning the body or cleaning surfaces. While wet wipes are very effective, selling them to consumers in a wetted state means that costs for transporting the wetting solution is passed onto the consumer. In times of increased awareness of energy costs, it is desirable to sell wipers in a dry state, and let the consumer add water or a desired solution to the wet wipe just prior to use. This is done in the prior art with facial cleansing cloths and the like.

The prior art cloths are generally planar in configuration, and sold in a folded form.

The consumer unfolds the cloths and wets them prior to use. If a consumer should choose to use one of the prior art cloths for cleaning skin or other surfaces that are unclean due to particulate matter, he or she will find that a planar cloth does not as easily pick up the particulate matter as a cloth towels with a textured surface. Thus, there is a need for a wiping substrate that is not only cost effective to transport, but is capable of picking up particulate matter more effectively than a wiper with a planar configuration.

SUMMARY

The present invention provides a method of making an article comprising the steps of: providing a planar substrate and stitching the planar substrate with a moisture sensitive shrinking filament. The stitching forms a pattern and the stitching is not displaced with respect to the planar substrate.

Another aspect of the present invention is a method of creating a three-dimensional article comprising the steps of: (a) providing a planar substrate; (b) stitching the planar substrate with a moisture sensitive shrinking filament, wherein the stitching forms a pattern, and wherein the stitching is not displaced with respect to the planar substrate;
(c) compressing the planar substrate into a pill configuration; and (d) applying an aqueous liquid to the planar substrate.

The present invention will now be described in detail with reference to embodiments illustrated in the accompanying drawings.

BRIEF DESCRIPTION OF DRAWINGS

These and other features, aspects, and advantages of the present invention will become better understood with regard to the following description, appended claims, and accompanying drawings where:

DETAILED DESCRIPTION

Figure 2:
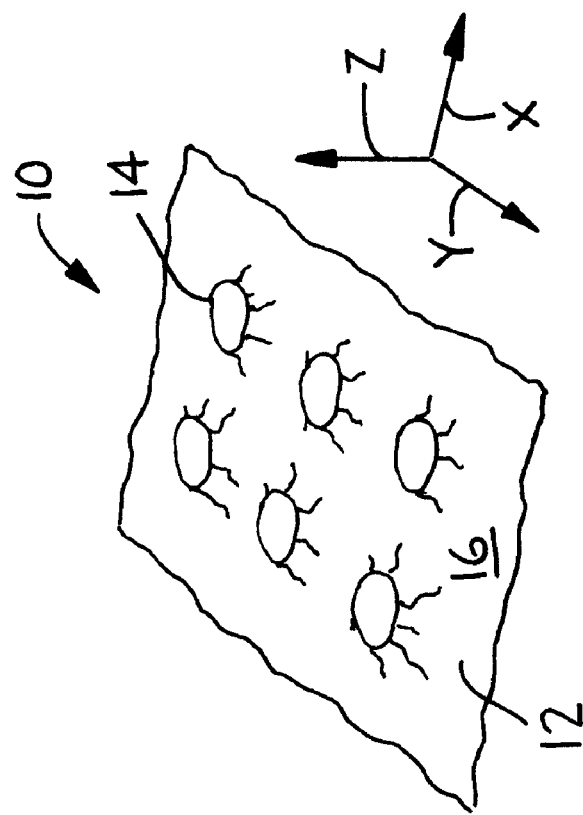
FIG. 2 is a view of the wiper of FIG. 1 shown in a wetted state.

While this specification concludes with claims particularly pointing out and distinctly claiming that which is regarded as the invention, it is anticipated that the invention can be more easily understood through reading the detailed description and study of the accompanying drawings.

Definitions

As used herein the term "nonwoven fabric or web" means a web having a structure of individual fibers or threads that are interlaid, but not in a regular or identifiable manner as in a knitted fabric. The term also includes individual filaments and strands, yarns or tows as well as foams and films that have been fibrillated, apertured, or otherwise treated to impart fabric-like properties. Nonwoven fabrics or webs have been formed from many processes such as for example, meltblowing processes, spunbonding processes, and bonded carded web processes.

As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns.

Spunbond material is made from spunbond fibers. As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as, for example, described in U.S. Pat. Nos. 4,340,563; 3,692,618; 3,802,817; 3,338,992; 3,341,394; 3,502,763; 3,502,538; and 3,542,615.

Spunbond fibers are quenched and generally not tacky when deposited onto a collecting surface. Spunbond fibers are generally continuous and have average diameters frequently larger than 7 microns, typically between about 10 and 20 microns.

Meltblown material is made from meltblown fibers. As used herein the term "meltblown fibers" means fibers formed by extruding a molten thermoplastic material through a plurality of fine, usually circular, die capillaries as molten threads or filaments into converging high velocity, usually heated, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface often while still tacky to form a web of randomly disbursed meltblown fibers. Such a process is disclosed, for example, in U.S. Pat. No. 3,849,241. Meltblown fibers are microfibers that may be continuous or discontinuous and are generally smaller than 10 microns in average diameter.

As used herein "bonded carded webs" or "BCW" refers to nonwoven webs formed by carding processes as are known to those skilled in the art and further described, for example, in U.S. Pat. No. 4,488,928, which is incorporated herein by reference. Briefly, carding processes involve starting with a blend of, for example, staple fibers with bonding fibers or other bonding components in a bulky ball that is combed or otherwise treated to provide a generally uniform basis weight. This web is heated or otherwise treated to activate the adhesive component resulting in an integrated, usually lofty nonwoven material.

As used herein the "moisture-activated shrinking filament" (filament 14) is a liquid-contractible material capable of shrinking upon contact with water.

EXAMPLES

Figure 1:
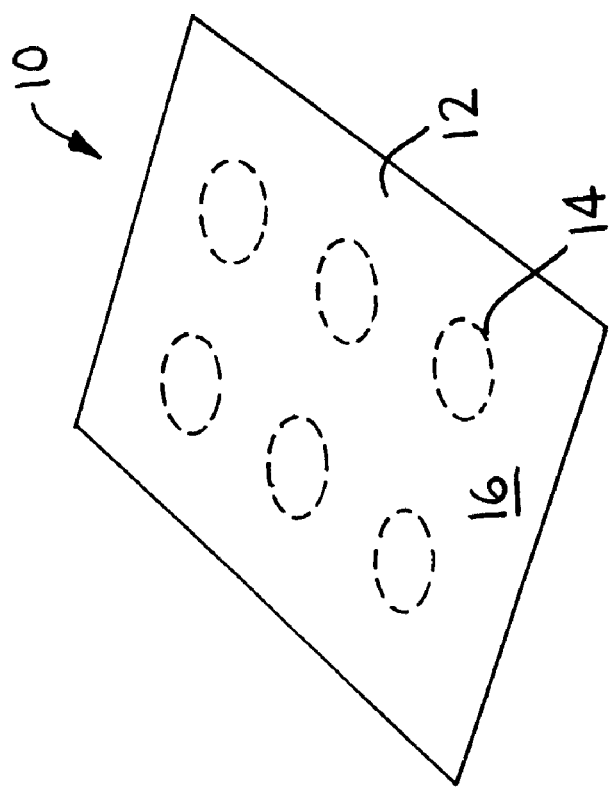
FIG. 1 is a top perspective view of one embodiment of the present invention shown in a dry state.

Although the present invention is equally applicable to other configurations such as being used as a top-sheet for bandages, liners, pads or diapers, a desired embodiment of an article of the present invention is a wiper such as that shown in FIG. 1. The use of the descriptor "wiper 10" is not meant to be limiting.

The wiper 10 of the invention includes a substrate 12 and a filament 14 that is applied to the substrate 12. When wetted with an aqueous liquid, filament 14 shrinks and gathers the substrate 12. Desirably, filament 14 is applied to the substrate 12 in a pattern such that the wiper 10 takes on a more three-dimensional configuration after wetting as opposed to a flat sheet configuration.

The fibers forming the substrate 12 can be made from a variety of materials. The choice of fibers depends upon, for example, the intended end use of the finished fabric and fiber cost. For instance, suitable fibrous substrates may include, but are not limited to, natural fibers such as cotton, linen, jute, hemp, wool, wood pulp, etc. Similarly, regenerated cellulosic fibers, such as viscose rayon and cuprammonium rayon, modified cellulosic fibers, such as cellulose acetate, or synthetic fibers, such as those derived from polypropylenes, polyethylenes, polyolefins, polyesters, polyamides, polyacrylics, etc., alone or in combination with one another, may likewise are used. Blends of one or more of the above fibers may also be used, if so desired. Among wood pulp fibers, any known papermaking fibers may be used, including softwood and hardwood fibers. Fibers, for example, may be chemically pulped or mechanically pulped, bleached or unbleached, virgin or recycled, high yield or low yield, and the like. Mercerized, chemically stiffened or crosslinked fibers may also be used.

Synthetic cellulose fiber types include rayon in all its varieties and other fibers derived from viscose or chemically modified cellulose, including regenerated cellulose and solvent-spun cellulose, such as Lyocell. Chemically treated natural cellulosic fibers can be used, such as mercerized pulps, chemically stiffened or crosslinked fibers, or sulfonated fibers. Recycled fibers, as well as virgin fibers, can be used. Cellulose produced by microbes and other cellulosic derivatives can be used. As used herein, the term "cellulosic" is meant to include any material having cellulose as a major constituent, and, specifically, comprising at least 50 percent by weight cellulose or a cellulose derivative. Thus, the term includes cotton, typical wood pulps, non-woody cellulosic fibers, cellulose acetate, cellulose triacetate, rayon, thermomechanical wood pulp, chemical wood pulp, debonded chemical wood pulp, milkweed, or bacterial cellulose.

In one embodiment of the present invention a cellulosic paper towel substrate is used. This substrate 12 may have a basis weight of about 30 grams or greater per square meter, a bulk of about 5 cubic centimeters or greater per gram, a geometric mean wet tensile strength of about 400 grams per three inches or greater, and a vertical absorbent capacity of about 4 grams of water or greater per gram of fiber. One specific example of a paper towel type substrate 12 is shown and described in U.S. Pat. No. 6,727,004 issued to Goulet et al. on Apr. 27, 2004, and is incorporated herein.

In another embodiment of the present invention a synthetic substrate 12 is used, similar to the substrate commonly used for wet wipes. For instance, the substrate 12 could be a nonwoven spunbond material, bonded carded web, meltblown material or the like. Examples of wet wipe substrates are disclosed in U.S. Pat. Nos. 6,683,143; 6,429,261; 6,815,502; 6,599,848; 6,444,214; 6,713,414; 6,548,592; 6,579,570; 6,653,406; and 6,537,663.

Desirably, regardless of the exact type of substrate that is used, the substrate 12 is sufficiently dimensionally stable and has a wet strength such that the substrate 12 will avoid collapsing when it is contacted with water. Desirably, when the products of this invention are saturated with water and crumpled and thereafter released, they quickly open up to mostly uncrumple themselves. Thus, it is desirable that substrate 12 exhibit an adequate wet strength.

As known in the art, various materials may be utilized to add additional wet strength to the substrate 12, should it be needed. Such wet strength agents are commercially available from a wide variety of sources and some of such agents are generally described in U.S. Pat. No. 5,779,860 issued to Hollenberg et al. Any material that, when added to a paper or tissue, results in providing a wet strength to dry strength ratio in excess of 0.1 will be considered a suitable wet strength agent. Such agents are generally classified as "permanent" or "temporary" wet strength agents. Permanent agents provide a product that retains more than 50% of its original wet strength after exposure to water for a period of at least five minutes; temporary agents provide a product that retains less than 50% of its original wet strength after exposure to water for five minutes. Such agents, whether permanent or temporary, are typically added to pulp fibers in an amount of at least about 0.1 dry weight percent, and usually in an amount of from about 0.1 to about 3 dry weight percent, based on the dry weight of the pulp fibers.

Suitable permanent wet strength agents that are of utility in the present invention are typically water soluble, cationic oligomeric or polymeric resins that are capable of either crosslinking with themselves (homocrosslinking) or with the cellulose or other constituent of the wood fiber. The most widely-used materials for this purpose are the class of polymer known as polyamide-polyamine-epichlorohydrin (PAE) type resins.

The temporary wet strength resins that can be used in connection with this invention include, but are not limited to, those resins that have been developed by American Cyanamid and are marketed under the name Parez 631 NC (now available from Cytec Industries, West Paterson, N.J.). This and similar resins are described in U.S. Pat. No. 3,556,932 issued to Coscia et al. and U.S. Pat. No. 3,556,933 issued to Williams et al. Other temporary wet strength agents that should find application in this invention include modified starches such as those available from National Starch and marketed as Co-Bond 1000. It is believed that these and related starches are covered by U.S. Pat. No. 4,675,394 issued to Solarek et al. Derivatized diaidehyde starches, such as described in Japanese Kokai Tokkyo Koho JP-A-03,185,197, should also find application as useful material is for providing temporary wet strength. It is also expected that other temporary wet strength materials such as those described in U.S. Pat. Nos. 4,981,557; 5,008,344 and 5,085,736 issued to Bjorkquist would be of use in this invention. With respect to the classes and the types of wet strength resins listed, it should be understood that this listing is simply to provide examples and that this is neither meant to exclude other types of wet strength resins, nor is it meant to limit the scope of this invention.

Although wet strength agents as described above find particular advantage for use in connection within this invention, other types of bonding agents can also be used to provide the necessary wet resiliency. They can be applied at the wet end or applied by spraying or printing, etc. after the substrate 12 is formed or after it is dried.

The substrate 12 of the present invention may be formed from a single layer or multiple layers. In the case of multiple layers, the layers are generally positioned in a juxtaposed or surface-to-surface relationship and all or a portion of the layers may be bound to adjacent layers. Nonwoven webs of the present invention may also be formed from a plurality of separate nonwoven webs wherein the separate nonwoven webs may be formed from single or multiple layers. In those instances where the nonwoven web includes multiple layers, the entire thickness of the nonwoven web may be subjected to a binder application or each individual layer may be separately subjected to a binder application and then combined with other layers in a juxtaposed relationship to form the finished nonwoven web.

Desirably, in one embodiment of the present invention, each wiper 10 is impregnated with a composition. Such compositions may be used to clean and/or condition a surface related to personal care or household care. In another embodiment of the present invention, microencapsulated beads or materials are added to the substrate 12 by known techniques. The microencapsulated beads can be formed to be soluble in a liquid, such as water. In this case, the microencapsulated beads will dissolve upon contact with the liquid and, upon being dissolved, will release the encapsulated material in the beads. The composition or materials in the microencapsulated beads can include an antibiotic, a pharmaceutical, an alcohol, a fragrance, an oil, a skin conditioner, a skin moisturizer, a heating or cooling compositions, warming and cooling agents, or combinations thereof. Other materials can include cleansers, polishes, anti-itch materials and anti-inflammatory materials.

In one example, the article 10 may include a surface active agent that may be soap or other ingredients. The surface active agent selected may include a soap, including a natural soap such as sodium stearate, preferably in the form of flakes or shavings and the like, but other forms also may be used and are within the scope of the present invention. A synthetic surface active agent such as sulfonated linear and branched hydrocarbons, alpha olefins or alklated aromatics and compatible salts thereof are also suitable for the article of the invention. Amine oxide and polyether alcohol surface active agents, either individually or in compatible combination with other surface active agents may also be preferred for particular applications. Additionally, fragrance materials and dyes or colorants, and foam enhancing agents such as diethanolamides and the like may be incorporated into wiper 10 of the present invention.

In yet another example, it may be preferred to select surface active agents having antimicrobial activity or to include antimicrobial agents either admixed with the surface active agents or as microencapsulants as described above. Suitable antimicrobial agents include, but are not limited to, quaternary ammonium salts, biguanides, halogenated phenols and the like. When the surface active agent and the antimicrobial agents are selected, care should be taken to ensure that the materials selected are compatible with each other and with the substrate materials. These materials may or may not be encapsulated.

Like substrate 12, the moisture-sensitive shrinking filament 14 may be made from various materials. For example, suitable materials for the filament 14 are liquid shrinkable filaments made from film, fiber, threads, foamed bodies, or the like.

Those materials capable of shrinking by 10% or more, or particularly 20% or more when exposed to an aqueous liquid are desirable. Materials such as this include modified cellulose fibers (e.g. cotton and rayon) such as carboxymethylated cotton methylated cotton, ethylated cotton, hydroxyethylated cotton, sulfated cotton, sulfonated cotton, phosphate cotton, cationic cotton, amphoteric cotton, sodium acrylate-, acrylic acid-, acrylonitrile- or acrylamides grafted cellulose fiber and crosslinked fiber thereof; wool or silk modified in the same manner as above; modified synthetic fiber, such as partially saponified acylonitrile series of fiber and vinilon fiber which is partially esterfied by maleic acid; and yarns made from these fibers. A desirable material for the first component is a yarn or filament available from Nitivy Company, Japan (SOLVRON Yarn—SHC Grade). This water shrinkable component is a polyvinyl alcohol filament.

The incorporation of the moisture sensitive shrinking filament 14 in the substrate 12 can be accomplished by sewing on a sewing machine using the filament as the needle thread, bobbin thread, or both. The sewing may be carried out in a manner of lock-stitching and the stitch length is approximately 1-10 mm. When the filament 14 is used as a needle or bobbin thread, the other thread may not always be a yarn capable of shrinking when wetted with an aqueous solution.

The incorporation of the filament 14 in the substrate 12 may also be accomplished by knitting using the filament 14 as a knitting yarn. Yet another method of incorporating the filament 14 into substrate 12 is by needle punching techniques. Any other method of uniting the filament 14 to the substrate 12 is appropriate. However, whatever method is used to unite the filament 14 to substrate 12, it is most desirable that the filament 14 not slide or shift in position with respect to the substrate 12. This way, when filament 14 shrinks, the substrate 12 will gather at the stitching lines.

Referring now to FIGS. 1 and 3-6, various stitching patterns may be used to create a three-dimensional wiper from a substantially planer material. Most generally, the stitching patterns fall into one of three categories: (a) a pattern made from discrete shapes (see FIG. 1), (b) a pattern made from stitching lines that cross-over one another (see, FIG. 4), and (c) a pattern made from stitching lines that do not cross over one another (see, FIGS. 3 and 5).

Referring now to FIG. 1, shown is a wiper 10 made from a nonwoven substrate 12 and a stitched pattern made with filament 14. This wiper 10 is in a dry, unstressed state. One will note that the stitched pattern is an array of discrete shapes, which in this example are circular. It is contemplated that the discrete shapes could be any other geometric shape such as a rectangle, oval, heart, holiday related shapes, baby related shapes, animal related shapes and the like. The discrete shapes may be all identical, or each shape could be different. The discrete shapes are spaced evenly as an array, or could be randomly located on the substrate surface 16. The spacing between each discrete shape is such that they do not overlap. Desirably, the discrete shapes are spaced apart by a distance that allows the substrate to gather therebetween.

Referring now to FIG. 2, the substrate of FIG. 1 is shown in a wetted state. The wetted filament 14 shrinks, but the substrate 12 does not shrink. This creates a puckering effect about each of the discrete shapes defined by filament 14. The puckering causes a dimension change, especially in the z-direction. What was once a flat, and effectively a two-dimensional substrate is now a puffy three-dimensional wipe. The advantage presented by a three-dimensional wipe is that it can more easily pick up particulates. Further, the filaments and gathers can be used to lightly exfoliate skin.

Figure 3:
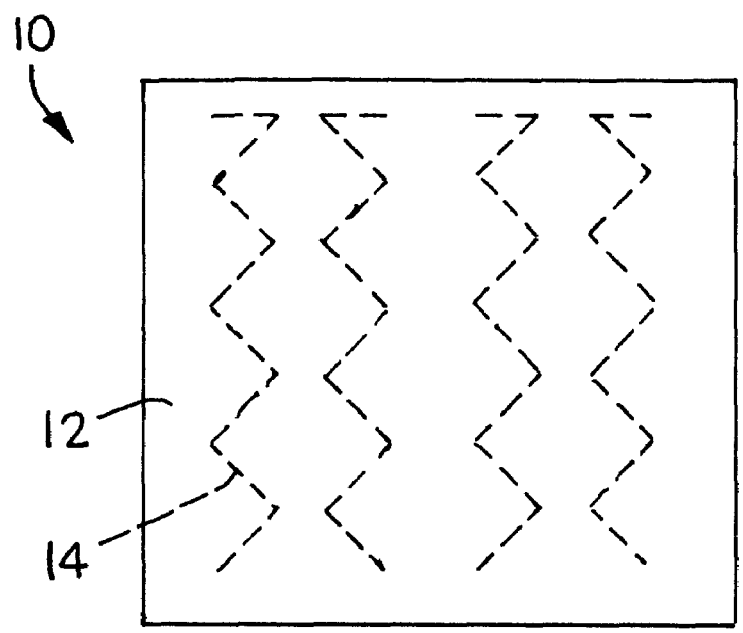
FIG. 3 is a plan view of a second embodiment of the present invention in a dry state.

Referring now to FIG. 3, shown is a plan view of another exemplary wiper 10. In this example, the filament 14 is stitched onto the substrate 12 in a repeating zig-zag pattern. None of the rows of zig-zag filament crosses another, and there is a space therebetween. Each zig-zag could be identical, or could be alternating right- and left-handed as shown. It is contemplated that other shapes such as lines or discrete geometric shapes could be intermingled with the zig-zag lines, if desired.

Any quilt pattern may be used.

Figure 4:
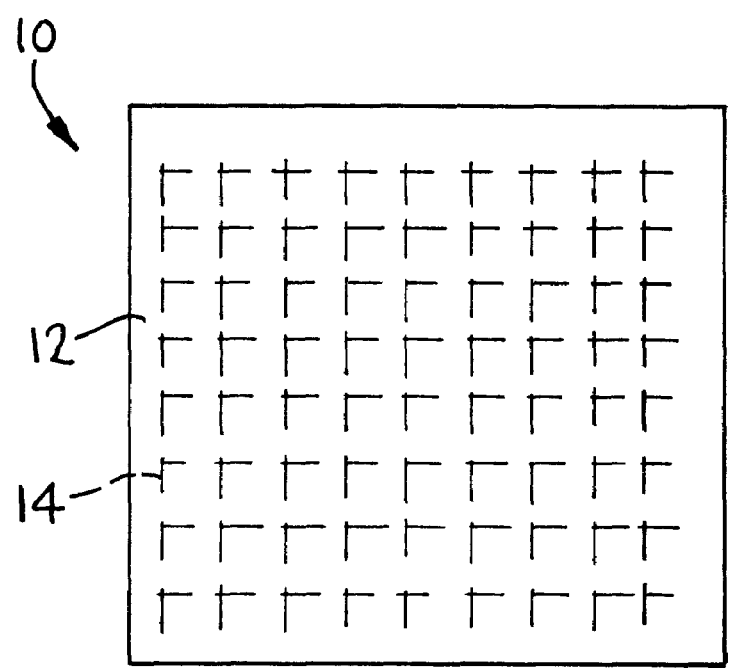
FIG. 4 is a plan view of a third embodiment of the present invention in a dry state.

Referring now to FIG. 4 is an example of a wiper 10 having a filament 14 pattern that overlaps. In this simple pattern, there is a grid defined by equally spaced lines of filament 14.

It is contemplated that the spacing could be not equally spaced to form an interesting pattern.

Figure 5:
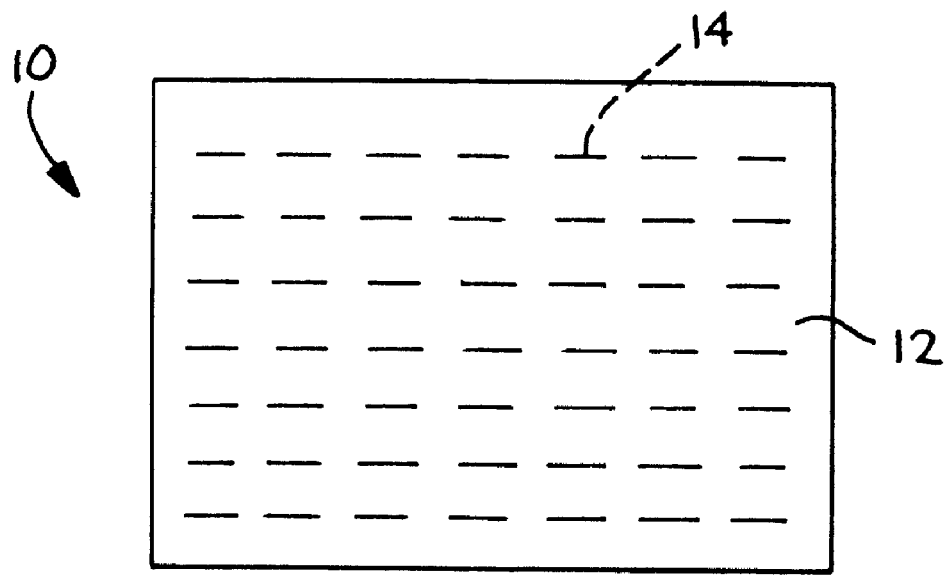
FIG. 5 is a plan view of a fourth embodiment of the present invention in a dry state.

Referring now to FIG. 5 is another example of a wiper 10 having linear rows of filament 14 placed thereon so that they do not overlap. While these rows are equally spaced, it is contemplated that a pattern could be formed from rows that are not equally spaced.

Figure 6:
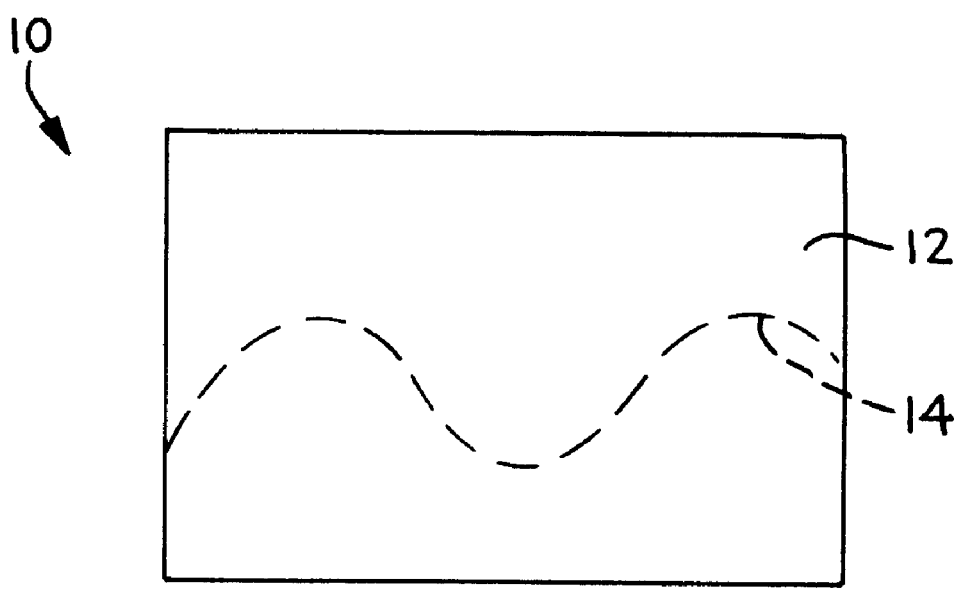
FIG. 6 is a plan view of a fifth embodiment of the present invention in a dry state.
Figure 9:
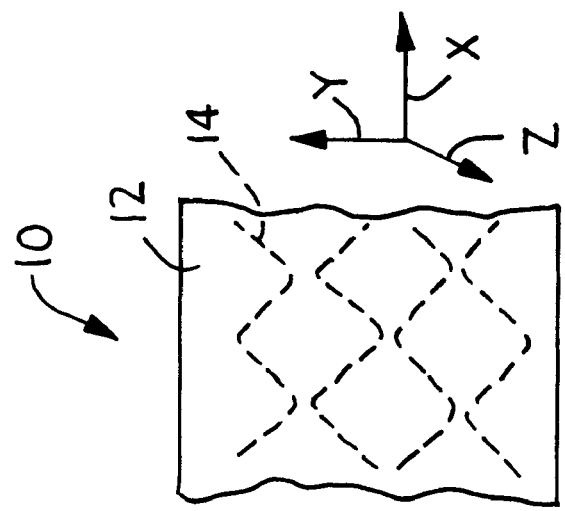
FIG. 9 is a plan view of the second embodiment of the present invention in a wetted state.

Referring now to FIG. 6 is a sine-wave pattern stitched thereon. While there is only one line of filament 14, it is contemplated that there could be several lines. The examples shown in FIGS. 1-6 are not meant to be limiting. Any quilt pattern could be used to create lines and discrete shapes. For example, a double wedding-ring pattern could be used. Any design, functional and/or aesthetic, is possible.

In one embodiment of the present invention, the wiper 10 is compressed to a smaller size using any known technique, the techniques including but not limited to submitting the wiper 10 to vacuum pressure. The compressed wiper 10 expands after being exposed to a liquid. The liquid can be any liquid that will de-compress the wiper 10 and cause the filament 14 to shrink. By way of example, the liquid could be water. The liquid in this case, also preferably dissolves the composition and/or microencapsulated beads. The result of the application of liquid is that the wiper 10 expands and the filaments 14 shrink thereby forming a three-dimensional wipe.

In accordance with another aspect of the present invention, the wiper 10 that is compressed can also be shaped. The wiper 10 can also have printed material on it. The shape of the wiper 10 and the printed material may have a relation to the wiper 10 and the composition or material released by the microencapsulated beads. For example, if the wiper 10 is a wash cloth and the microencapsulated material is a floral fragrance, the wiper 10 can be shaped like a flower and a picture of the flower can be printed on the wiper 10.

A method for making a compressed wiper 10 that is expandable to a larger size upon contact with water includes selecting a compressible material. In accordance with one aspect of the present invention, the material can be selected from the group consisting of woven fabric and non-woven material. The selected material can be optionally formed into a preselected shape. Suitable methods for forming the material include, but are not limited to, cutting, shearing, tearing and the like.

The method of the invention further includes applying a preselected amount of a suitable non-encapsulated material to the compressible material. The non-encapsulated material can be a surface active agent, with or without other additives as described above, that is applied to the compressible substrate.

The method then includes reducing the physical size of the compressible substrate by application of sufficient mechanical force to compress the substrate material. This compression may also be facilitated by conducting the compression at a temperature above room temperature but below a decomposition point for the selected materials and/or under an atmosphere of pressure below that of ambient atmospheric pressure and/or substantial absence of moisture. Depending on the material, the compression can also be accomplished by applying a vacuum.

In addition to compressing the material, for some applications, the method may include the compressed material being wrapped with a packaging material to retain the compressed size. Suitable wrapping materials may include a metallic foil wrap, a paper wrapper, a polymeric film wrap, a heat shrinkable wrapper and a wrap formed from combinations of these materials. Depending on the materials selected for the substrate and the additives, it may be preferred that the wrapping materials substantially prevent atmospheric moisture transmission to the packaged article.

Figure 8:
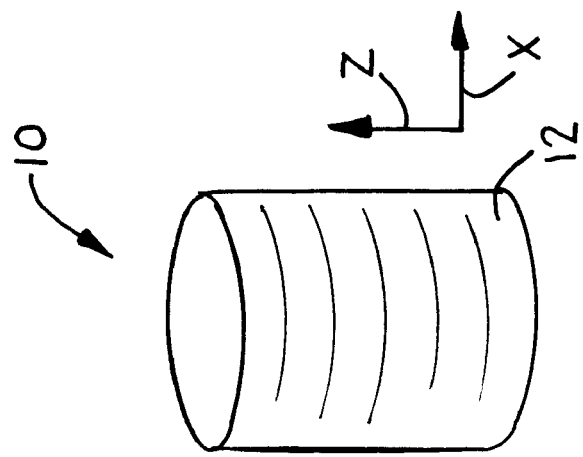
FIG. 8 is a front perspective view of the wiper of FIG. 7 almost immediately after being wetted.
Figure 7:
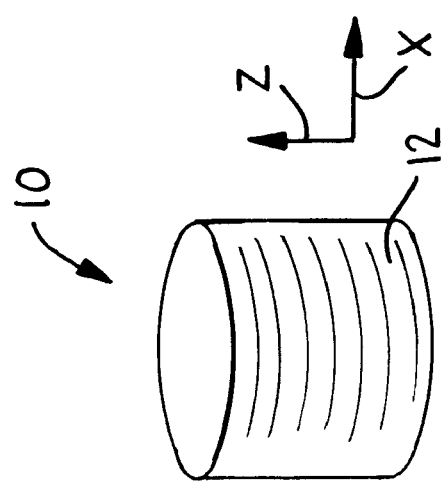
FIG. 7 is a front perspective view of a wiper of the present invention in a dry compressed state.

In order to use compressed wiper 10 of the invention, a user would unwrap the article from the package and allow it to become wet with water, whereupon the compressed article would absorb water and expand. For example, the compressed wiper 10 shown in FIG. 7 will expand at least in the z-direction when wetted with an aqueous liquid, see FIG. 8. Eventually, the wiper 10 will be fully expanded and the filament 14 shrunk so that wiper 10 is ready for used. In the desired instance where article 10 includes a surface active agent, the user may be able to generate a foam or lather, by rubbing the wiper 10 on a surface with water for cleaning and the like.

A particular benefit of article 10 of the invention would be to provide dense well-packaged cleaning articles that could be readily stored because they are compressed. Desirably, the article includes surface active agents.

While particular embodiments of the present invention have been illustrated or described, it would be obvious to those skilled in the art that various other changes and modifications can be made without departing from the spirit and scope of the invention. For example, the wiper 10 could be used as a liner in a pad or diaper. Further, it should be apparent that all combinations of such embodiments and features are possible and can result in preferred executions of the invention. Therefore, the appended claims are intended to cover all such changes and modifications that are within the scope of the invention.

The invention claimed is:

1. A method of creating a three-dimensional article comprising the steps of:
    (a) providing a planar substrate;
    (b) stitching the planar substrate with a moisture sensitive shrinking filament;
    wherein the stitching forms a pattern, and wherein the stitching is not displaced with respect to the planar substrate;
    (c) compressing the planar substrate into a pill configuration; and
    (d) applying an aqueous liquid to the planar substrate.

2. The method according to claim 1 wherein the steps are carried out in the following order: a, b, c, and d.

3. The method according to claim 1 wherein the stitching pattern comprises a plurality of discrete shapes.

4. The method according to claim 1 wherein the stitching pattern comprises shapes that are formed by a first stitch line crossing over a second stitch line.

5. The method according to claim 1 wherein the stitching pattern comprises shapes that are formed by stitching lines that do not cross one another.

6. The method according to claim 1 wherein the moisture sensitive shrinking filament comprises polyvinyl alcohol.

* * * * *